US00PP36371P2

(12) United States Plant Patent
Li

(10) Patent No.: US PP36,371 P2
(45) Date of Patent: Jan. 7, 2025

(54) *VERBENA* PLANT NAMED 'KLEVP23139'

(50) Latin Name: ***Verbena* x *hybrida***
Varietal Denomination: KLEVP23139

(71) Applicant: KLEMM + SOHN GMBH & CO. KG, Stuttgart (DE)

(72) Inventor: Ruijun Li, North Parramatta (AU)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/639,199

(22) Filed: Apr. 18, 2024

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./263.1, 308
See application file for complete search history.

(56) References Cited

U.S. PATENT DOCUMENTS

PP28,320 P2 * 8/2017 Li ..... A01H 6/86
Plt./308

* cited by examiner

*Primary Examiner* — Karen M Redden
(74) *Attorney, Agent, or Firm* — Weatherly IP Solutions, LLC; James M. Weatherly

(57) ABSTRACT

A new *Verbena* plant particularly distinguished by a red flower colour with white eyes; round growth habit; and good earliness, is disclosed.

1 Drawing Sheet

Genus and species: *Verbena* x *hybrida*.
Variety denomination: 'KLEVP23139'.

BACKGROUND OF THE NEW PLANT

The present invention comprises a new and distinct variety of *Verbena*, botanically known as *Verbena* x *hybrida*, and hereinafter referred to by the variety name 'KLEVP23139'. 'KLEVP23139' originated from a cross-pollination conducted in October 2020 in Cobbitty, New South Wales, Australia between the proprietary female *Verbena* variety '17.70.52' (unpatented), and the proprietary male *Verbena* variety '16.60.49' (unpatented).

The seeds from the cross were sown and plants were grown for evaluation, where an individual plant designated 'KLEVP23139' was selected from the group of plants in Cobbitty, New South Wales, Australia in October 2020.

In October 2020, 'KLEVP23139' was first vegetatively propagated by vegetative cuttings in Cobbitty, New South Wales, Australia. 'KLEVP23139' was found to reproduce true to type in successive generations of asexual propagation via vegetative cuttings.

SUMMARY

The following are the most outstanding and distinguishing characteristics of this new variety when grown under normal horticultural practices in Cobbitty, New South Wales, Australia.

1. Red flower colour with white eyes;
2. Round growth habit; and
3. Good earliness.

DESCRIPTION OF THE PHOTOGRAPH

This new *Verbena* plant is illustrated by the accompanying photograph which shows the plant's overall plant habit including form, buds, foliage, and flowers. The photograph is of a plant approximately 12-weeks-old grown indoors in Stuttgart, Germany in May 2022. The colors shown are as true as can be reasonably obtained by conventional photographic procedures.

DESCRIPTION OF THE NEW VARIETY

The following detailed descriptions set forth the distinctive characteristics of 'KLEVP23139'. The data which define these characteristics were collected from asexual reproductions carried out in Cobbitty, New South Wales, Australia. Data was collected on three-month-old plants grown in 2020. Color references are to The R.H.S. Colour Chart of The Royal Horticultural Society of London (R.H.S.), 5$^{th}$ edition (2007).

Classification:
- *Family*.—Verbenaceae.
- *Botanical*.—*Verbena* x *hybrida*.
- *Common*.—*Verbena*.
- *Designation*.—'KLEVP23139'.

Parentage:
- *Female parent*.—'17.70.52' (unpatented).
- *Male parent*.—'16.60.49' (unpatented).

Plant:
- *Growth and branching habit*.—Upright with a compact and round shape.
- *Height* (*from top of soil*).—24.5 cm.
- *Width* (*horizontal plant diameter*).—34.0 cm.
- *Time to produce a finished flowering plant*.—Approximately 8 weeks.
- *Time to initiate and develop roots*.—7 to 9 days.
- *Root description*.—RHS 155B (White), fine fibrous roots.

Stems:
*Number of branches per plant.*—More than 24.
*Growth habit.*—Upright.
*Length.*—21.0 cm.
*Diameter.*—0.28 cm.
*Internode length.*—2.2 cm.
*Color.*—RHS 139D.
*Anthocyanin.*—Absent.
*Texture and appearance.*—Pubescent.

Leaves:
*Arrangement.*—Opposite.
*Immature and mature leaf.*—Color: Upper surface: RHS 141A. Lower surface: RHS 141C.
*Length.*—4.3 cm.
*Width.*—2.1 cm.
*Shape.*—Lanceolate.
*Apex.*—Acute.
*Base.*—Obtuse.
*Margin.*—Crenate.
*Texture.*—Upper surface: Leathery. Lower surface: Rugose.
*Venation type.*—Pinnate.
*Venation color.*—Upper surface: RHS 141D (Green). Lower surface: RHS 141D (Green).
*Petioles.*—Length: 0.3 cm. Diameter: 0.1 cm. Color: RHS 141D (green). Texture: Leathery.

Flower buds:
*Shape.*—Tall, cylindrical.
*Length.*—1.5 cm.
*Diameter.*—0.3 cm.
*Color (at tight bud).*—RHS 58C.

Inflorescence:
*Blooming habit (flowering season).*—Continuously.
*Lastingness of individual blooms on the plant.*—About a week.
*Fragrance.*—None detected.
*Inflorescence type.*—Umbel.
*Length of inflorescence.*—4.6 cm.
*Diameter of inflorescence.*—5.0 cm.
*Number of florets per inflorescence.*—20.
*Peduncle.*—Color: RHS 141A (green). Length: 2.1 cm. Diameter: 0.2 cm.

Florets:
*Length.*—2.0 cm.
*Diameter.*—2.6 cm.
*Texture.*—Smooth.
*Form.*—Single.
*Color.*—Immature: Upper surface: RHS 45C with white eyes (RHS 155C). Lower surface: RHS 46D with white eyes (RHS 155D). Mature: Upper surface: RHS N57A with white eyes (RHS 155C). Lower surface: RHS 58C with white eyes (RHS 155D).
*Corolla tube length.*—1.8 cm.
*Corolla tube color.*—RHS 157B.
*Petals.*—Length of lobe: 1.8 cm. Diameter of lobe: 0.7 cm. Lobe shape: Obtuse. Apex: Emarginate. Base: Fused. Margin: Entire. Texture: Upper surface: Glossy, satiny. Lower surface: Glossy, satiny.
*Pedicels.*—Not visible.

Sepals:
*Shape.*—Lanceolate.
*Apex.*—Acute.
*Base.*—Fused.
*Margin.*—Entire.
*Length.*—1.3 cm.
*Diameter.*—0.2 cm.
*Color.*—RHS 141C.
*Texture.*—Upper surface: Hairy, dull. Lower surface: Hairy, dull.

Reproductive organs:
*Stamens.*—Present.
*Quantity.*—4.
*Color.*—RHS 139D.
*Filament length.*—0.3 cm.
*Filament diameter.*—0.1 cm.
*Anther.*—Shape: Elliptic. Color: RHS 141D. Length: 0.15 cm. Diameter: 0.1 cm.
*Pollen amount.*—Sparse.
*Pistils.*—Number: 1. Length: 1.6 cm. Diameter: 0.1 cm. Stigma: Color: RHS 141D. Appearance: Ovate. Length: 0.1 cm. Diameter: 0.1 cm. Style: Color: RHS 141D. Length: 1.7 cm. Diameter: 0.1 cm. Appearance: Long.

Fruit and seed set: To date, fruit and seed development have not been observed on plants.

Disease and pest/insect resistance: Plants of KLEVP23139 have been observed to tolerate to powdery mildew (*Podosphaera xanthii*).

COMPARISON WITH PARENTAL LINES AND KNOWN VARIETY

'KLEVP23139' is distinguished from its parents as described in Table 1.

TABLE 1

| Comparison with Parental Lines | | | |
|---|---|---|---|
| Trait | Variety 'KLEVP23139' | Female parent '17.70.52' | Male Parent '16.60.49' |
| Flower color | Red with white eyes | Red | Bicolor: red and pink |

'KLEVP23139' is most similar to the commercial *Verbena* variety 'KLEVP15616' (U.S. Plant Pat. No. 28,320). Differences between the varieties are described in Table 2.

TABLE 2

| Comparison with Similar VarietyTrait | Variety 'KLEVP23139' | Commercial line 'KLEVP15616' |
|---|---|---|
| Flower colour | Red with white eyes | Salmon pink with red center |
| Growth habit | Round | Upright |
| Earliness | Earlier than 'KLEVP15616' | Later than 'KLEVP23139' |

I claim:

1. A new and distinct variety of *Verbena* plant designated 'KLEVP23139' as illustrated and described herein.

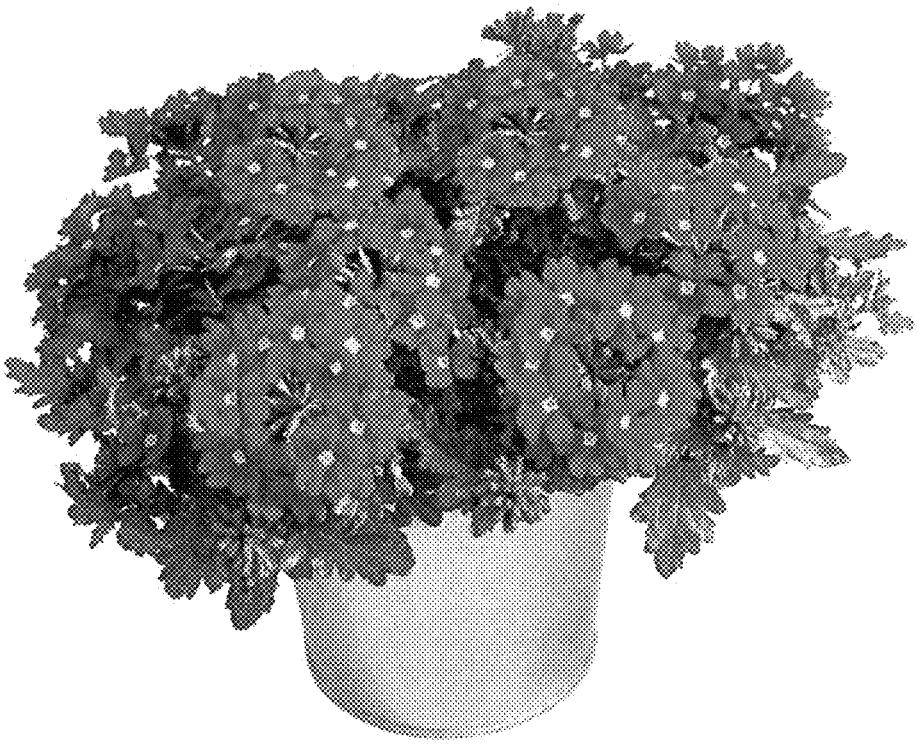

* * * * *